(12) United States Patent
Kurzban

(10) Patent No.: US 10,449,080 B2
(45) Date of Patent: Oct. 22, 2019

(54) FACIAL ALIGNMENT SYSTEM

(71) Applicant: Scott Kurzban, West Hills, CA (US)

(72) Inventor: Scott Kurzban, West Hills, CA (US)

( * ) Notice: Subject to any disclaimer, the term of this patent is extended or adjusted under 35 U.S.C. 154(b) by 352 days.

(21) Appl. No.: 15/159,612

(22) Filed: May 19, 2016

(65) Prior Publication Data

US 2016/0338869 A1 Nov. 24, 2016

Related U.S. Application Data

(60) Provisional application No. 62/164,478, filed on May 20, 2015.

(51) Int. Cl.
*A61F 5/08* (2006.01)
*A61B 34/10* (2016.01)
*A61B 90/00* (2016.01)

(52) U.S. Cl.
CPC ............... *A61F 5/08* (2013.01); *A61B 34/10* (2016.02); *A61B 2034/108* (2016.02); *A61B 2090/065* (2016.02)

(58) Field of Classification Search
CPC ........... A61F 5/08; A61F 5/01; A42B 3/18–20
See application file for complete search history.

(56) References Cited

U.S. PATENT DOCUMENTS

| | | | | |
|---|---|---|---|---|
| 850,978 A * | 4/1907 | Soars | ................... | A61F 5/08 602/17 |
| 1,100,991 A * | 6/1914 | Rostow | ................... | A61F 5/08 602/17 |
| 1,372,089 A * | 3/1921 | Rostow | ................... | A61F 5/08 602/17 |
| 1,378,455 A * | 5/1921 | Hilgers | ................... | A61F 5/08 602/17 |
| 3,742,943 A * | 7/1973 | Malmin | ................... | A61F 5/08 606/204.45 |
| 4,621,378 A | 10/1986 | Hatchman | | |
| 4,774,935 A * | 10/1988 | Aronsohn | ................ | A61F 5/30 128/97.1 |
| 5,177,882 A | 1/1993 | Berger | | |
| 5,181,331 A | 1/1993 | Berger | | |
| 5,325,613 A | 7/1994 | Sussmann | | |
| 5,357,654 A * | 10/1994 | Hsing-Chi | ............. | A42B 3/145 2/418 |
| 5,502,902 A | 4/1996 | Sussmann | | |
| 5,511,325 A | 4/1996 | Hieblinger | | |
| 5,628,772 A * | 5/1997 | Russell | .................... | A61F 7/10 601/112 |
| 8,032,993 B2 | 10/2011 | Musal | | |

(Continued)

FOREIGN PATENT DOCUMENTS

CN 204951280 1/2016

OTHER PUBLICATIONS

International Search Report and Written Opinion issued in PCT/US2016/033346.

*Primary Examiner* — Jonathan A Hollm
(74) *Attorney, Agent, or Firm* — Jeffer Mangels; Butler & Mitchell LLP; Brennan C. Swain, Esq.

(57) ABSTRACT

A facial alignment system that includes a first mask portion and a rear portion. The rear portion includes a tightening mechanism mounted thereon that includes first and second tightening members that extend from the rear portion to the mask portion. The first and second tightening members are configured to exert a tightening force on the first mask portion.

12 Claims, 7 Drawing Sheets

(56) References Cited

U.S. PATENT DOCUMENTS

| | | | |
|---|---|---|---|
| 2010/0042139 A1* | 2/2010 | Honegger | A61F 5/08 606/204.45 |
| 2012/0174287 A1 | 7/2012 | Lemke | |
| 2013/0118500 A1 | 5/2013 | Stevens | |
| 2014/0163445 A1* | 6/2014 | Pallari | A61K 8/0212 602/43 |
| 2014/0261430 A1 | 9/2014 | Davis | |

* cited by examiner

FACIAL ALIGNMENT SYSTEM

CROSS REFERENCE TO RELATED APPLICATIONS

This application claims the benefit of U.S. Provisional Application No. 62/164,478, filed May 20, 2015, which is incorporated by reference herein in its entirety.

FIELD OF THE INVENTION

The present invention relates generally to a facial alignment system, and more particularly to a system for realigning the nose or other facial features.

BACKGROUND OF THE INVENTION

Currently, rhinoplasty is the only way to deal with any form of nasal reconstruction. Patients generally undergo rhinoplasty due to either nasal deformity or a desire for improved appearance. Deformity may be the result of an accident, genetics, or even a birth defect. In any case, rhinoplasty is a surgical procedure involving all of the common associated surgical risks and recovery time. Patients are often left with severe bruising around the eyes, commonly referred to as "panda eyes," with full recovery generally taking up to one year. Many patients try to hide the surgery from friends and family or refer to it as surgery to heal a "deviated septum" to disguise their true intentions. Lastly, patients are sometimes unhappy with the end result but left with little choice but to accept it, as the procedure is "all or nothing." If the patient is truly unhappy, they can go through a second procedure, after waiting a sufficient time for the effects of the first procedure to heal, and start the process all over again. See U.S. Pat. No. 3,742,943, the entirety of which is incorporated by reference herein, which discloses a mask for showing the appearance of the nose after rhinoplasty.

While rhinoplasty is the most common surgery to address facial imperfections or deformity, it is not the only such procedure. In addition to rhinoplasty, there are surgeries to improve the appearance of the cheeks, chin, forehead, and eye sockets. Similar surgeries and associated risks exist for these procedures.

Other devices or methods for reshaping the nose are also known. For example, see U.S. Pat. No. 850,978 and U.S. Publication No. 2010/0042139, the entireties of which are incorporated by reference herein.

SUMMARY OF THE PREFERRED EMBODIMENTS

In accordance with a first aspect of the present invention there is provided a facial alignment system that includes a first mask portion and a rear portion. The rear portion includes a tightening mechanism mounted thereon that includes first and second tightening members that extend from the rear portion to the mask portion. The first and second tightening members are configured to exert a tightening force on the first mask portion. In a preferred embodiment, the first and second tightening members are removably attached to the first mask portion. Preferably, the system includes at least a second mask portion and the first and second tightening members are configured to be removably attached to the second mask portion.

In a preferred embodiment, the first mask portion includes first and second connection members. The first tightening member is connected to the first connection member and the second tightening member is connected to the second connection member. Preferably, the tightening mechanism includes a rotary dial and when the rotary dial is rotated the first and second tightening members are pulled, thereby placing pressure on the user's face (and preferably the feature to be aligned or moved). Preferably, the first mask portion includes at least a first pressure zone that places pressure on the feature to be aligned or moved. If a second mask portion is included, the second mask portion includes a first pressure zone in the same location as the first mask portion. However, the first pressure zone on the second mask portion has been modified to move the feature to be aligned or moved even further than the first mask portion. In a preferred embodiment, the first mask portion includes a nose portion and the first pressure zone is located in the nose portion. In an embodiment, the first mask portion includes a second pressure zone that is not located in the nose portion. In another embodiment, the first pressure zone can be located outside of the nose and the nose portion can be omitted.

In a preferred embodiment, the facial alignment system includes a pressure measurement system that includes at least one measurement device secured to an inner surface of at least one of the first mask portion and the rear portion. The at least one measurement device can be positioned in a pressure zone on the first mask portion.

In accordance with another embodiment of the present invention there is provided a method that includes obtaining a mask assembly that includes a first mask portion and a rear portion and activating a tightening mechanism that causes first and second tightening members to exert a tightening force on the first mask portion. The tightening mechanism is mounted on the rear portion and includes the first and second tightening members extending from the rear portion to the mask portion. In a preferred embodiment, the tightening mechanism includes a rotary dial, and the method includes rotating the dial to pull the first and second tightening members.

In a preferred embodiment, the first mask portion includes first and second connection portions and the first tightening member is removably connected to the first connection portion and the second tightening member is removably connected to the second connection portion. The method further includes disconnecting the first tightening member from the first connection portion, disconnecting the second tightening member from the second connection portion, obtaining a second mask portion that includes a third and fourth connection portions, connecting the first tightening member to the third connection portion, and connecting the second tightening member to the fourth connection portion.

In accordance with another embodiment of the present invention there is provided a method that includes modeling a patient's head to provide a first model, making a first change to a first feature on the first model to provide a second model, and creating a first mask portion using the second model. The first mask portion includes a first pressure zone in a first state. In a preferred embodiment, the method also includes making a second change to the first feature on the second model to provide a third model, and creating a second mask portion using the third model. The second mask portion includes the first pressure zone in a second state.

In a preferred embodiment, the step of modeling the patient's head includes the steps of taking a mold of the patient's head and creating the first model using the mold. The step of making a second change to the first feature on the second model to provide a third model can be accomplished by physically making a change to the second model to alter it to become the third model (i.e., the second and third models are physically the same model, but with changes) or it can be accomplished by creating a new model from the original mold, but with changes between the second model and the third model.

In another preferred embodiment, the step of modeling the patient's head includes the step of scanning or measuring the patient's head and providing the first model using computer software. The second and third models are created by altering the first model as desired and 3-D printing or otherwise creating the first and second mask portions.

The present invention is a non-invasive system and method to address minor to moderate facial abnormalities or imperfections that a person may want to correct. The invention incorporates the process and the apparatus for performing the process that generates a desired result for the patient and migrates the patient's appearance to a target state through the use of at least one and preferably a series of facial masks or mask portions (that are part of a mask assembly), each with slightly different contours, to address the imperfection or issue that the patient desires to change. In use, the mask portions apply pressure through the use of straps or other tightening mechanisms or means by which the mask portion is tightened to or against the patient's face. It will be appreciated by those of ordinary skill in the art that slight changes are made to the nose and facial features through the use of each mask portion, culminating in a final mask portion that conforms the patient's face to the target state that the patient desired. In use, the patient can wear the mask assembly when they are sleeping. In another embodiment, the mask assembly can be worn during the day or at other times when the patient is awake. It should be appreciated that the process may be sped up by wearing the mask assembly more frequently throughout the day.

To start the procedure, the patient visits a practitioner/representative (e.g., a doctor) for an initial consultation. During the initial consultation, the patient discusses what they wish to accomplish by the procedure and the doctor/representative assesses initial suitability for the procedure. The doctor/representative takes the necessary photographs, mold(s) and/or computer image(s) of the patient's face and/or head. The images are then evaluated to develop a proposed target state appearance of the patient's nose and face based on the patient's stated objectives. The target state is then discussed with the patient and either approved or modified based on patient feedback. Once approved, specialists design the necessary series of mask portions to achieve the desired result. Any number of mask portions is within the scope of the present invention. It will be appreciated that the number of mask portions depends on the final result and the amount of change that is necessary. A single mask portion may be used. Patients can see the progress with each mask portion and are even able to see the incremental change during the period of time that each individual mask portion is being worn. A patient may stop the procedure at any time if they are happy with the incremental result.

It will be appreciated by those of ordinary skill in the art that the process works by reshaping the cartilage and/or bones of the nose and/or other facial features through direct and indirect, positive and negative pressure applied through the use of the mask portions. In a preferred embodiment, the final mask portion is retained for future use by the patient in case of injury or for continuing or ongoing treatment to reinforce the final state (similar to a retainer used for teeth after braces).

In a preferred embodiment, the invention includes software for developing the masks. To start the process, digital images are taken of the patient's face from multiple angles and uploaded into the software. In addition to the digital images being taken, measurements can be taken of the patients face and head and entered into the software, either directly from the measuring equipment or through hand keyed entry. The software combines the images and measurements together to produce a three dimensional (3-D) rendering of the patient's face. Based upon the patient's stated goals, the 3-D rendering is modified to achieve the desired results. The specialist(s) use the software to make the required adjustments. In a preferred embodiment, to aid the specialist and to obtain consistent results, the software has certain standard corrective actions that may provide a starting point. Such starting points may include, but are not limited to, eliminating a bump on the surface of the nose or narrowing the nose. Once the target state is approved by the patient, the software is used to construct the multiple stage mask portions between the current state and the target state. In a preferred embodiment, the software has a Computer Aided Design component (CAD) that creates the schematics for the multiple mask portions. The software bases the number of masks portions, or stages, on the extent and amount of movement required to achieve the desired appearance. It will be appreciated that the greater the amount of movement necessary the more stages that are likely necessary. The software is programmed with a standard maximum targeted movement for each mask, but can be modified as needed to allow for more or less movement, depending on each unique situation. Each stage created by the software is used to create a different mask portion. Each incremental stage has a minor deviation from the previous stage in order to migrate the nose or other facial feature towards the target state, culminating in the final mask that will conform to the patient's target state appearance.

As described below, instead of or in addition to using the 3-D scanner and software, a mold can be taken of the patient's face. The mold can then be used to create a model of the patient's face and head. If a single mask portion is required, the head model can then be modified and the first mask portion can be created or cast using the modified head model. If more than one mask portion is required, the head model can be modified to a first state and the first mask portion can be created thereon. Then, the head model can be modified to a second state and the second mask portion can be created thereon. This can be done in stages until the final mask portion (which is of the target state) is created. In another embodiment, multiple head models can be created for each of the different mask portions created.

In another exemplary process in accordance with the present invention, first, the patient gets their face and head measured either by a traditional mold or by a 3-D scanner. If a manual mold is used, a present state head model is developed. If a 3-D scanner is used, the measurements are transmitted to software. Next, if the manual mold was created, the nose on the model is revised manually to recast for the shaping masks, developing the interim and final mask portions. If the scanner was used, the image is manipulated and revised through the use of software to develop the interim and end states or mask portions. Next, with the manual mold, the mask portions are then cast and produced. If the scanner was used, the mask portions are then 3-D printed or otherwise produced.

It will be appreciated that each of the mask portions preferably includes attachment points or connection portions for the back portion that includes the tightening mechanism.

The back portion with the tightening mechanism may be hard plastic, like the mask portion or may be more malleable or bendable. The back portion preferably extends around from the back of the head toward or to the temples on either side of the head and to a spot behind or below the ear, allowing for the wires or straps of the tightening mechanism to attach to the mask portion. For example, the tightening mechanism can include two sets of double wires or U-shaped wires on each side that can be pulled tight, similar to the tightening mechanism taught in U.S. Pat. No. 5,511,325 (the "'325 patent"), the entirety of which is incorporated by reference herein. In another embodiment, the tightening mechanism may include plastic straps, similar to the tightening mechanism taught in U.S. Pat. No. 8,032,993, the entirety of which is incorporated by reference herein. In this embodiment, the plastic straps would inset through slots on the mask and extend towards the back of the head and into the tightening mechanism to be cinched in. Generally, in a preferred embodiment, the tightening mechanism includes a rotary dial or the like that converts rotational motion to linear motion, which pulls the straps or wires to tighten the mask portion against the patient's face. Other tightening mechanisms are taught in U.S. Pat. Nos. 5,502,902, 5,325,613, 5,181,331 and 5,177,882, the entireties of which are incorporated by reference herein. In another embodiment, a second tightening mechanism is included. The first or second tightening mechanism can be a rotary tightening mechanism or a set of straps.

In a preferred embodiment, the mask assembly, and preferably the back portion, includes a pressure measuring system to measure the pressure being applied to the mask portion by the tightening system. The measurement system can be accessed by plugging a cable (e.g., mini or micro USB cable) into a receiver or port on the back portion to provide the doctor and/or the patient with the measurement readout. In another embodiment the measuring system can be wireless (e.g., bluetooth). In an embodiment, the readout can be a mobile phone. For example, a mobile application can be downloaded to the user's phone to provide the relevant pressure or force readout criteria. The mobile application may include charts or tables instructing the user the proper amount of pressure to be used on certain days and, based on the stage in the process (i.e., which mask portion and pressure is being applied), can present the user with a visual image of the user's progress.

As discussed above, the series of mask portions include variations or "steps" to migrate the patient's nose from the current state to the desired or target state. In some cases the patient will only need one mask portion while in more extreme cases, multiple mask portions will be necessary. It will be appreciated that the masks contact the nose at the point that is to be moved, thus applying pressure thereto. As the nose conforms to each mask it will be migrated to a final state.

BRIEF DESCRIPTION OF THE DRAWINGS

Like numerals refer to like parts throughout the several views of the drawings.

DETAILED DESCRIPTION OF THE PREFERRED EMBODIMENTS

Figure 1:
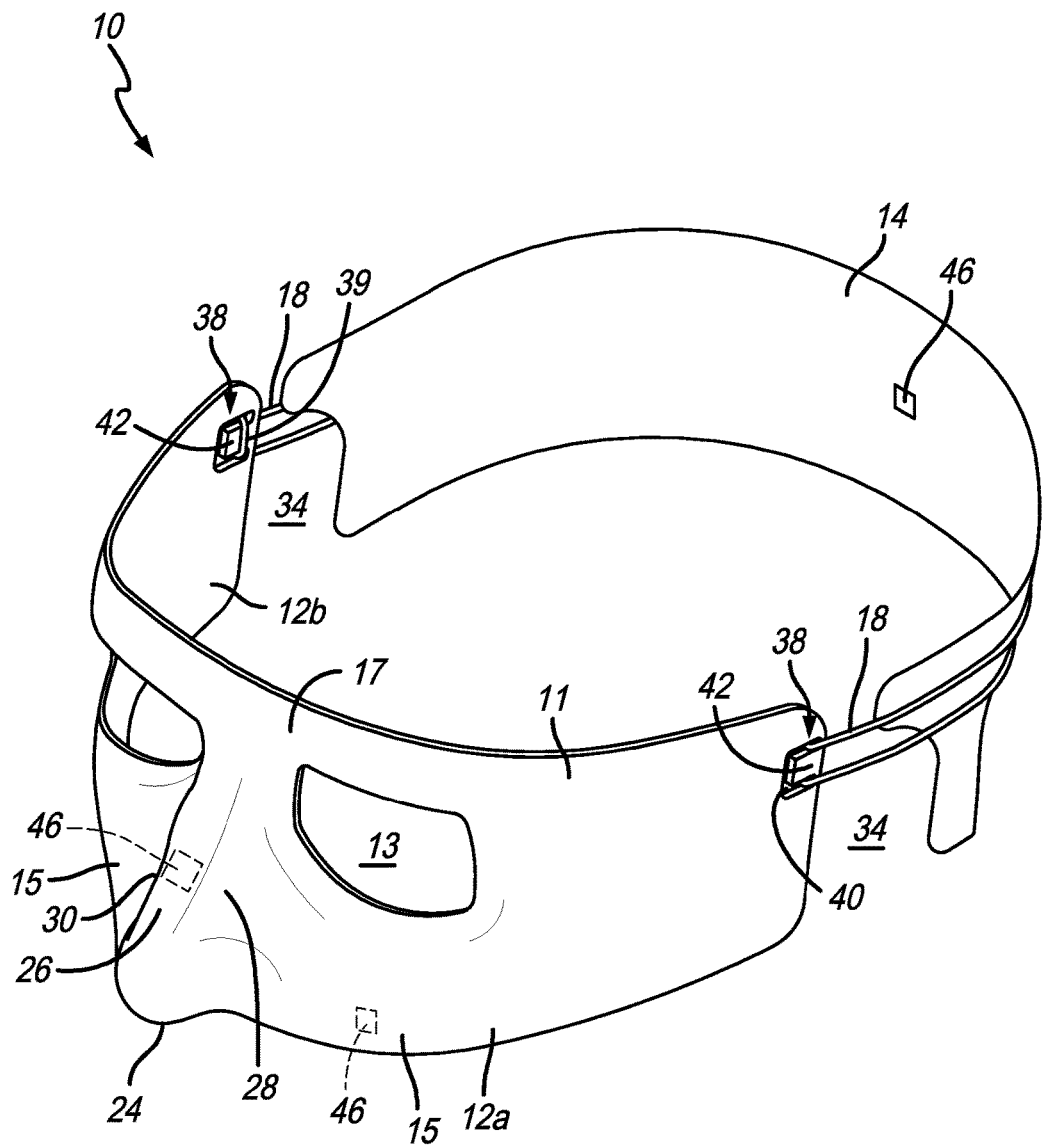
FIG. 1 is a perspective view of a mask assembly in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments.

Reference in this specification to "one embodiment" or "an embodiment" means that a particular feature, structure, or characteristic described in connection with the embodiment is included in at least one embodiment of the-disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

The present invention is a facial alignment system that includes a mask assembly 10 for applying pressure to a patient or wearer's face to reshape or align portions or zones on the wearer's face. Generally, the mask assembly 10 is used to reshape the wearer's nose. However, as described below, the mask assembly 10 can be used to align or reshape other areas of the wearer's face, such as the cheeks, areas around the eyes, forehead, chin etc. The mask assembly 10 will be described first and the facial alignment system that may include multiple mask portions or mask assemblies will be described thereafter.

Figure 2:
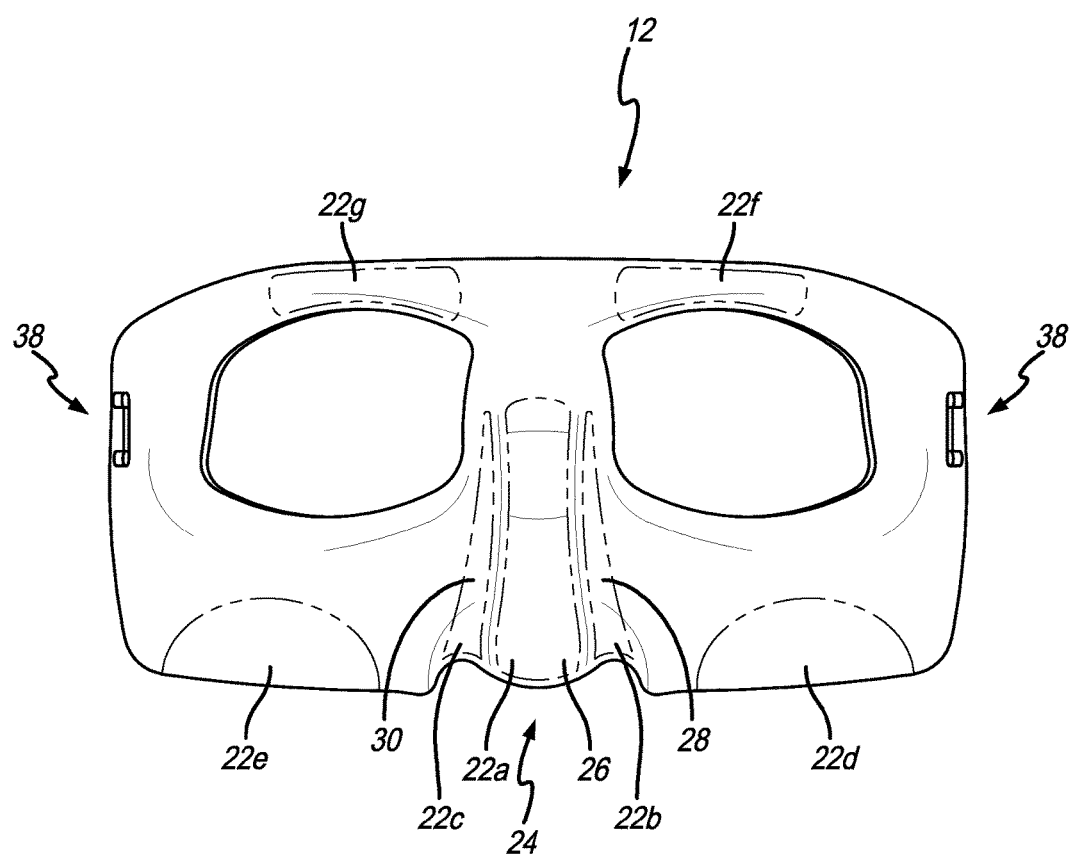
FIG. 2 is a front elevational view of the mask assembly of FIG. 1.
Figure 3:
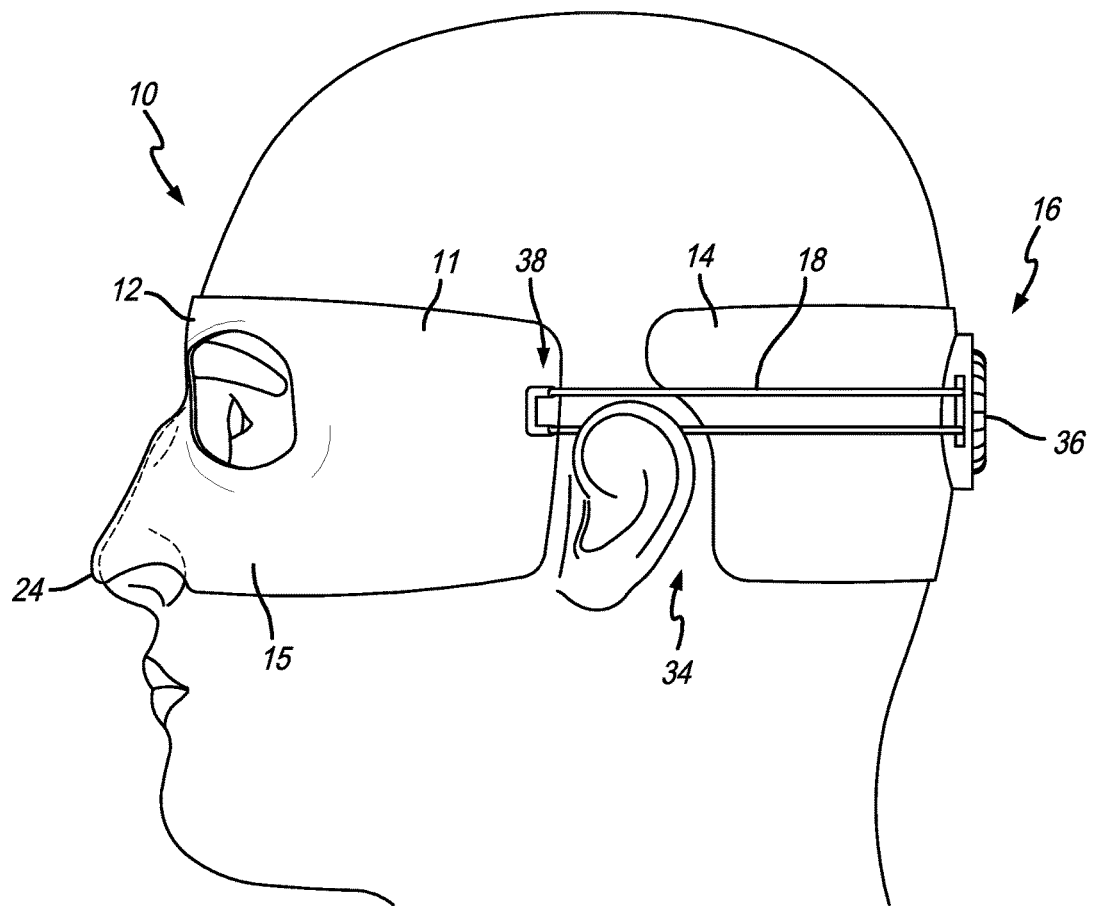
FIG. 3 is side elevational view of a user wearing the mask assembly of FIG. 1.
Figure 6:
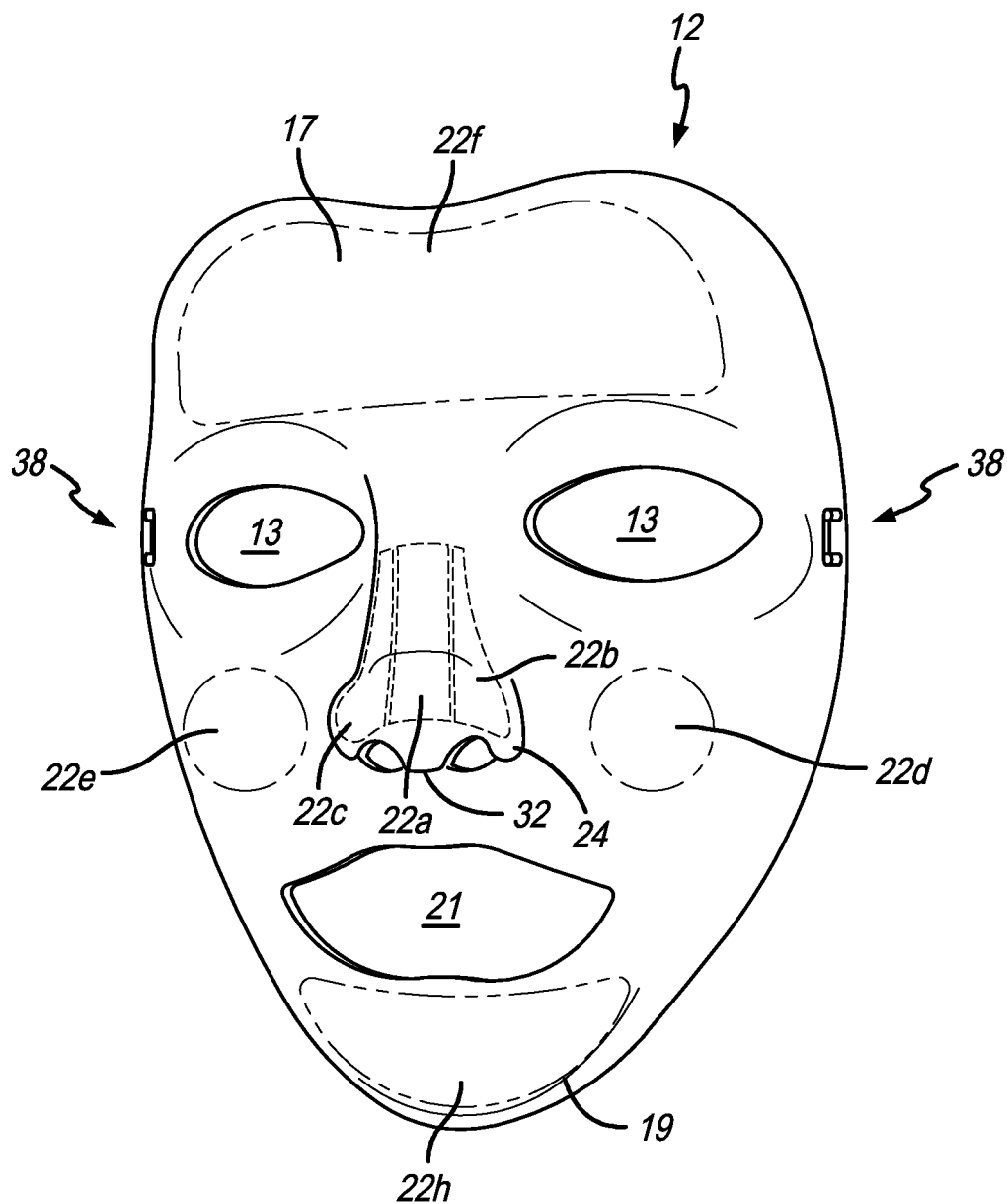
FIG. 6 is a perspective view of a mask portion in accordance with another preferred embodiment of the present invention.
Figure 7:
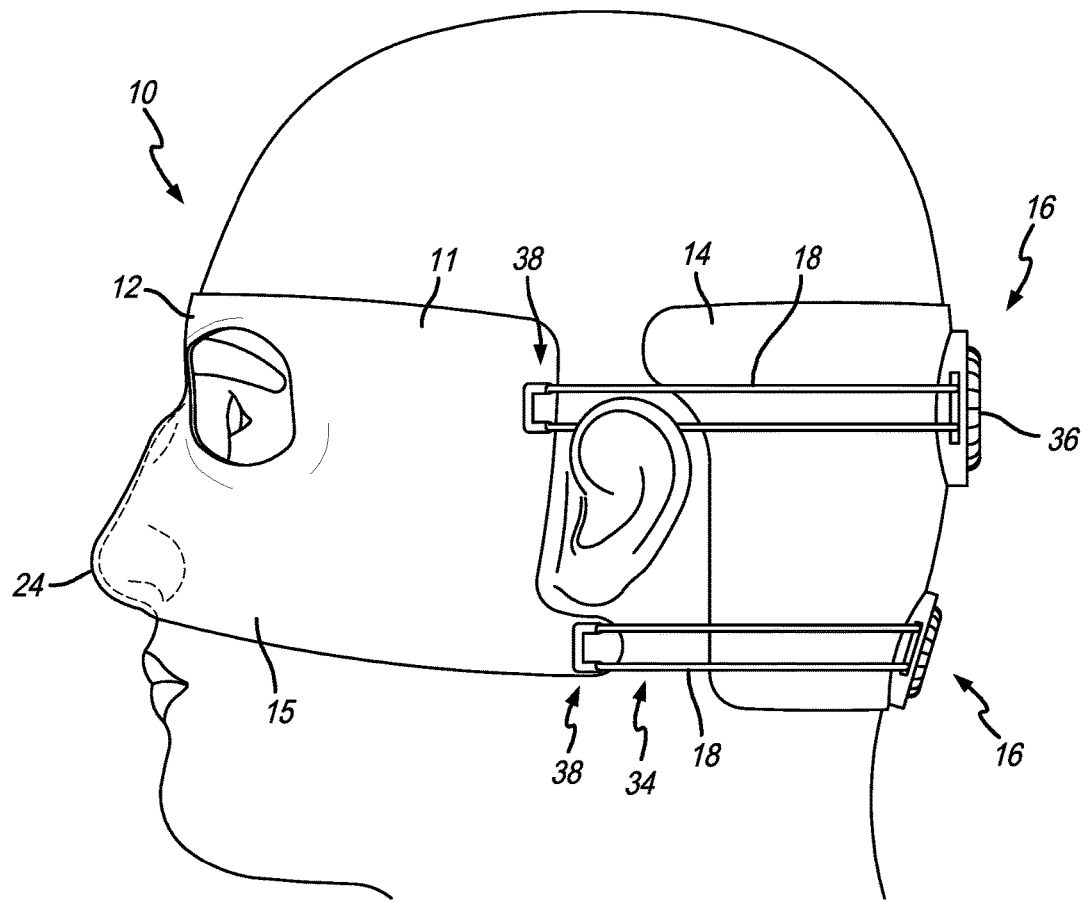
FIG. 7 is a side elevational view of a mask assembly that includes two tightening mechanisms in accordance with another preferred embodiment of the present invention.

As shown in FIGS. 1-3, the mask assembly 10 generally includes a mask portion 12, a rear portion 14, a tightening mechanism 16 and at least first and second tightening members 18. The mask portion 12 generally includes a main body portion 11, eye holes 13, a nose portion 24, cheek portions 15 and a forehead portion 17. The mask portion 12 also includes an inner surface 12a and an outer surface 12b, covers at least a portion of the user's face and can be any desired size. The mask portion 12 shown in FIG. 1 covers the user's nose, and eyes, and extends partially onto the forehead and cheeks. As shown in FIG. 6, in another embodiment, the mask portion 12 can extend below and around a user's mouth and over the chin and include a chin portion 19 and a mouth opening 21. It will be appreciated that the mask portion 12 includes at least one pressure zone 22. The pressure zones 22 are shown in FIGS. 2 and 7 on the mask portion 12 in dashed lines. The pressure zones are identified herein generally by the numeral "22." In embodiments with multiple pressure zones each zone is identified by the numeral "22" together with a letter (e.g., first pressure zone 22a, second pressure zone 22b, third pressure zone 22c, fourth pressure zone 22d, fifth pressure zone 22e, sixth pressure zone 22f, seventh pressure zone 22g, eighth pressure zone 22h, etc.). It will be appreciated that the pressure zones shown in the figures are only exemplary and any area of the mask can be a pressure zone if desired and if modified from the original state of the patient.

In a preferred embodiment, as shown in FIG. 1, the nose portion includes a front wall 26, a left side wall 28 and a right side wall 30. The nose portion 24 can also include a bottom portion 32, as shown in FIG. 6. In this embodiment, the bottom portion 32 preferably includes one or more nostril openings therein.

Figure 4:
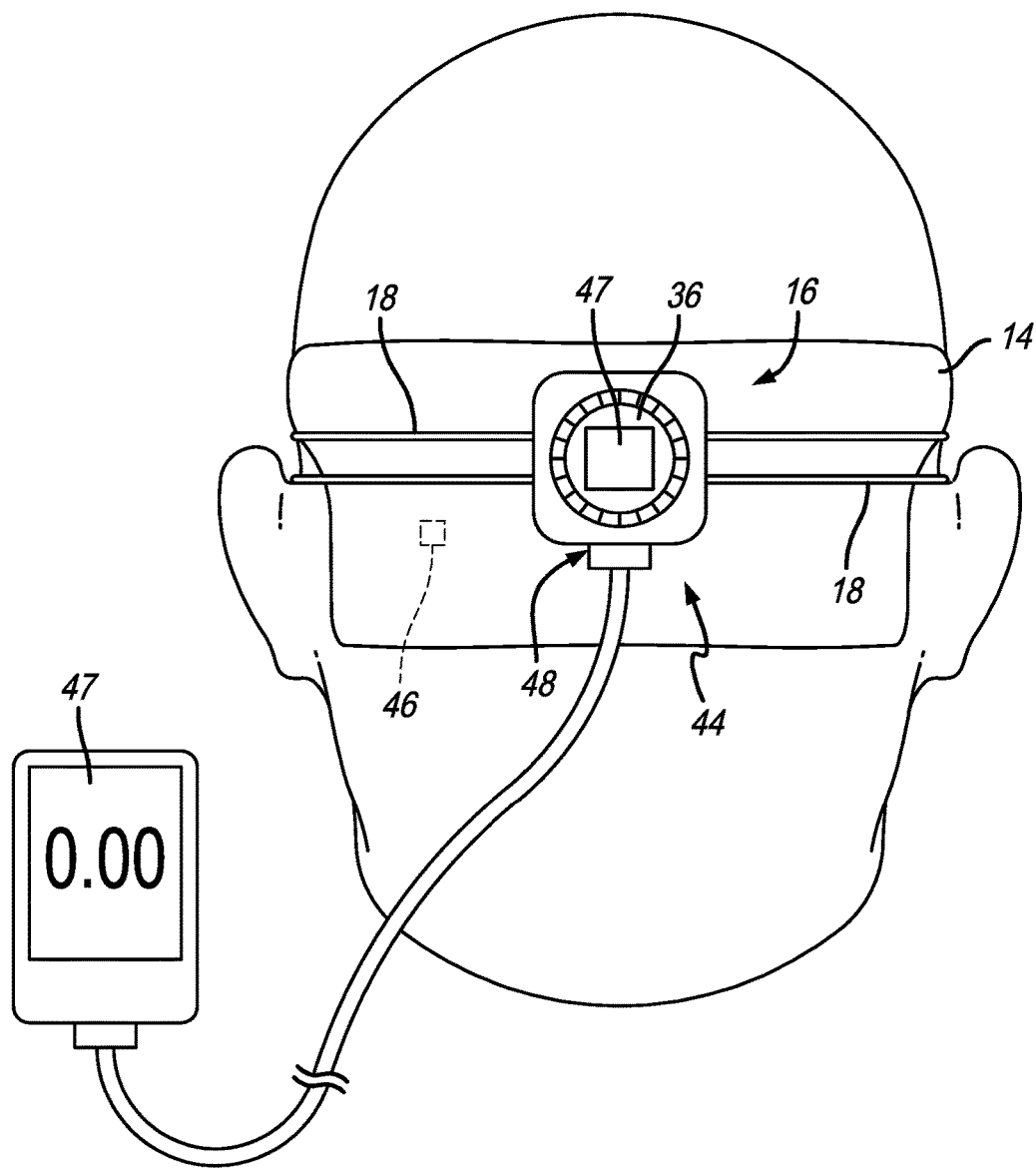
FIG. 4 is rear elevational view of a user wearing the mask assembly of FIG. 1.

As shown in FIGS. 3 and 4, in a preferred embodiment, the rear portion 14 extends over a significant portion of the posterior area of the user's cranium. A channel 34 is defined between the rear portion 14 and the mask portion 12. The first and second tightening members span the channel 34 and extend from the rear portion 14 to the mask portion 12. The tightening mechanism 16 is preferably mounted on the rear portion 14. In another embodiment multiple tightening mechanisms 16 can be included (see FIG. 7). In another embodiment, a single tightening mechanism can tighten more than 2 tightening members. However, in another embodiment, the tightening mechanism 16 (or tightening mechanisms) can be mounted on the mask portion 12 or the tightening mechanism 16 can be included on a separate side portion. Preferably, the rear portion 14 covers the user's occipital bone and covers some or all of the crown of the posterior portion of the users head or cranium.

Generally, the first and second tightening members 18 are configured to exert a tightening or pulling force on the mask portion 12. In a preferred embodiment, the tightening mechanism 16 includes a rotary dial 36 that when rotated pulls the first and second tightening members 18 (and narrows channel 34). In other words, the rotary dial 36 converts rotational motion to generally linear motion. Any type of rotary tightening mechanism is within the scope of the present invention. For example, the first and second tightening members can be connected to each other or to the rear portion 14 via Velcro, snaps, buttons, posts that snap into an opening (similar to those on a baseball hat or helmet), buckles, clamps. A number of other rotary tightening mechanisms are discussed above. Any mechanism that allows the first and second tightening members 18 to adjustably apply a tightening force or pressure on the mask portion 12 is within the scope of the present invention. Combinations of any of the tightening mechanisms described herein are also within the scope of the present invention.

The first and second tightening members 18 connect to first and second connection members or portions 38 on the mask portion 12. Anything that allows the first and second tightening members 18 to connect to the mask portion 12 is within the scope of the present invention. In a preferred embodiment, the first and second tightening members 18 are generally U-shaped wires 39 that extend from the tightening mechanism 16 and are connected to the first and second connection portions 38. As shown in the figures, in a preferred embodiment, the first and second connection portions 38 comprise a channel 40 defined in the mask portion 12 that forms a tab 42. On each side, the wire 39 is looped around the tab 42 to provide the connection between the first and second tightening members 18 and the first and second connection portions 38. In the embodiment shown in FIG. 3, the tab 42 is formed within the planes of the outer and inner surfaces of the mask portion 12. In another embodiment, the tab 42 can extend outwardly from the mask portion 12. For example, the connection member can be a hook, post, button, protrusion or the like. In other embodiments, the connection portions can be snaps that are attached to or molded into the mask portion and connect to a complementary snap on the tightening members, or the connection portions can be slots and the tightening members can extend through the slots and wrap back to the rotary dial.

In use, when the tightening mechanism 16 is operated the first and second tightening members 18 are pulled, thereby pulling on the mask portion 12 as a result of the connection of the first and second tightening members 18 to the first and second connection portions 38. In the embodiment shown in the drawings, when the rotary dial 36 is rotated, the first and second tightening members 18 are pulled rearwardly, thereby pulling on the tabs 42, which pulls the mask portion 12 rearwardly. This causes the various pressure zones 22 to place pressure on the user's face. It will be appreciated that the rotary type tightening mechanism allows the pressure to be adjusted in small increments, which can be beneficial for the alignment or reshaping described herein.

In a preferred embodiment, the mask assembly 10 includes a pressure measurement system 44 that measures the amount of pressure being applied by at least one of the mask portion 12 and the rear portion 14 to the user's head. More specifically, the pressure measurement system 44 allows the user or practitioner to monitor or know how much pressure is being applied to the user's face and the various pressure zones 22. The pressure measurement system 44 includes at least one or a plurality of sensors or measuring devices 46. For example, the measuring device 46 can be a differential pressure sensor, a strain gauge pressure sensor, a capacitance pressure transducer or sensor, a piezoelectric pressure transducer or sensor or the like. The measuring device 46 can be electrically communicated with a display 47 or readout that displays the pressure being exerted. The display 47 can be located on rear portion 14 or can be remote. In the embodiment shown in the figures, the pressure measurement system 44 includes a port 48. In this embodiment, a cord is connected to the port 48 and the pressure readout or display 47 is included on the opposite end of the cord so that the user can read the pressure measurement while wearing the mask assembly 10.

In an embodiment, one or more measuring devices 46 can be mounted on the inner surface of the rear portion 14 and/or on the inner surface of the mask portion 12. For example, a separate measuring device 46 can be placed in each of the pressure zones 22. Each of the measuring devices 46 can include a separate readout or a single readout can be provided for the measuring device 46 that has the highest pressure reading. In another embodiment, a single measuring device 46 can be placed on the inner surface of the rear portion 14. In another embodiment, the pressure measurement can be based on the tension in the first and second tightening members 18. In this embodiment, a measuring device can be associated with or located in the tightening device.

Figure 5C:
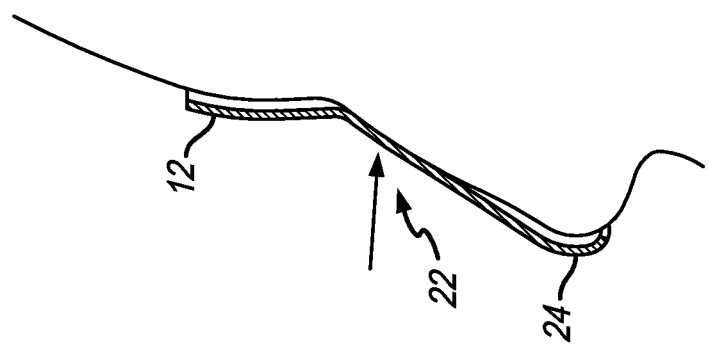
FIGS. 5A-5C show cross-sections of the nose portions of a series of mask assemblies in use to reduce the bump on a user's nose.
Figure 5B:
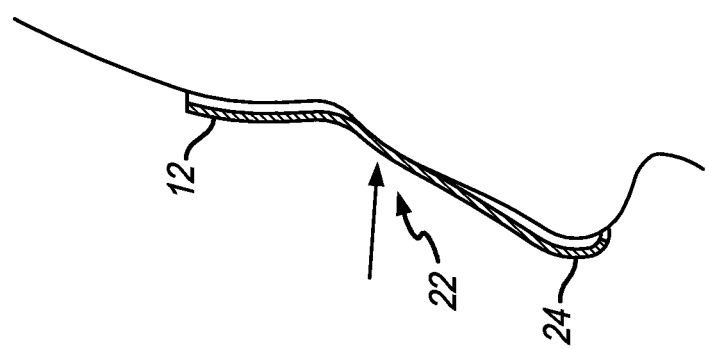
Figure 5A:
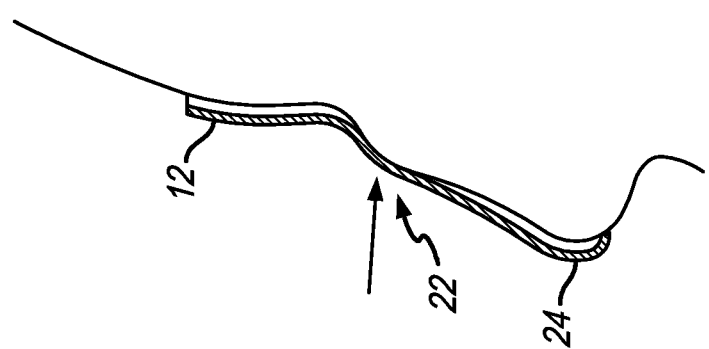

As discussed above, a single mask portion 12 (referred to herein as a first mask portion 12) can be used for a single treatment or multiple mask portions 12 can be used to bring a facial feature into a desired position. Also, multiple pressure zones can be included on the single mask (e.g. alignment of the nose to the left and shaping a dorsal hump on the nose). FIGS. 5A-5C show an exemplary use of three different mask portions 12 to reduce the bump on a user's nose. A cross-section of the nose portion 24 is shown in each of the figures.

To create the mask portions 12, a user or patient first has their face measured using a mold or 3-D scanner, as described above. Next, in the embodiment where a mold is used, a present state head model is created. Using the example shown in FIGS. 5A-5C, the bump on the nose of the head model is reduced and a first mask portion 12 is created or cast (see FIG. 5A). Next, the bump on the nose of the head model is further reduced and a second mask portion 12 is created or cast (see FIG. 5B). Next, the bump on the nose of the head model is further reduced to the final desired position and a third mask portion 12 is created or cast (see FIG. 5C).

If a 3-D scanner is used, the measurements of the user's face are transmitted to software to provide an image. Using the example shown in FIGS. 5A-5C, the image of the user's face is revised to reduce the bump on the nose and a first mask portion 12 is created or printed (see FIG. 5A). Next, the image of the user is revised to further reduce the bump on the nose and a second mask portion 12 is created or printed (see FIG. 5B). Next, the image of the user is revised to further reduce the bump on the nose to the final desired position and a third mask portion 12 is created or printed (see FIG. 5C).

It will be appreciated that the various pressure zones 22 are created in the mask portion 12 by a change being made to the head model or image. For example, if the user desires a change to their right cheek and the head model or image is manipulated to provide this change, a pressure zone 22 will be created in the mask portion 12. Therefore, in the example provided above, a pressure zone 22 is created by the front wall 26 of the nose portion 24 pressing on the bump on the user's nose.

In a preferred embodiment, multiple mask portions 12 are interchangeable with a single rear portion 14. In this embodiment, the first and second tightening members 18 are removably or releasably connected to the first and second connecting portions 38. This allows the first and second tightening members 18 to be disconnected from the first and second connecting portions 38 on the first mask portion 12 and then reconnected to the first and second connecting portions 38 on the second mask portion 12. In this embodiment, a single rear portion 14 (together with the tightening mechanism 16 and the first and second tightening members 18) can be provided with at least first and second mask portions in a kit (the head model and/or 3-D scanner and associated software and printer and materials for making the mask portions can also be included in the kit). In another embodiment, the first and second tightening members 18 can be permanently connected to the mask portion 12. In this embodiment, if multiple mask portions are needed multiple mask assemblies 10 are used. In another embodiment, the rear portion 14 can also be created using a head model or 3-D scanner.

An exemplary use of the system by a patient after the mask assembly and various mask portions have been created will now be described. The mask assembly 10 may already have the first mask portion 12 connected to the rear portion 14. If it is not, the first and second tightening members 18 are connected to the first and second connection portions 38 on the first mask portion 12. The user then places the mask assembly 10 over his/her head and positions the first mask portion 12 over his/her face (which includes facial features in the initial or current state). The tightening mechanism 16 is then activated. As a result, the inside surface of the first mask portion 12 contacts the user's face (and applies pressure thereto) in the desired pressure zones 22. This is done by turning the rotary dial 36 to thereby pull on the first and second tightening members 18, which exert a pulling force on the first mask portion 12. If the mask assembly 10 includes a pressure measurement system 44, the user rotates the rotary dial 36 to tighten or loosen the first mask portion 12 until the proper amount of pressure (as shown on the display) is applied. The amount of pressure may be an amount as desired by the user or may be specified by the user's practitioner or doctor. For example, the doctor may provide a chart that includes incremental pressures that are applied on subsequent days or the like before switching to a second mask portion or until the procedure is complete.

If a second mask portion 12 is included, after the first mask portion 12 has been used to move the desired facial feature(s) to completion (referred to herein as a first interim state), the first tightening member 18 is disconnected from the first connection portion 38 and the second tightening member 18 is disconnected from the second connection portion 38. In the embodiment shown in the figures, this is done by disconnecting the looped wire 39 from the tab 42 and moving the wire 39 out of the channel 40. The first tightening member 18 is then connected to the first connection portion 38 (referred to in the claims as the third connection portion) on the second mask portion 12 and the second tightening member 18 is connected to the second connection portion 38 (referred to in the claims as the fourth connection portion) on the second mask portion 12. Once again, the mask assembly 10 (with the second mask portion 12 thereon) is donned by the user and tightened appropriately until the facial feature(s) are moved to a second interim state. This procedure is repeated for each subsequent mask portion 12 until the facial feature(s) are moved to the target or final state. In another embodiment, some of the tightening members can be removable or disconnectable and other can be permanent. For example, a top strap can be used that are removable (such as shown in the pictures and a bottom strap can be elastic and permanently attached or removable. Elastic tightening members can be used anywhere.

It will be appreciated that the first and second tightening members may be a single wire or strap that connects to the tightening mechanism 16. In another embodiment, the tightening members may be elastic straps that are permanently or temporarily connected from the mask portion 12 to the rear portion 14. In another embodiment, the tightening mechanism may be mounted on the mask portion and the first and second tightening members may extend rearwardly to the rear portion 14.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

The teachings of the disclosure provided herein can be applied to other systems, not necessarily the system described above. The elements and acts of the various embodiments described above can be combined to provide further embodiments. Any measurements described or used herein are merely exemplary and not a limitation on the present invention. Other measurements can be used. Further, any specific materials noted herein are only examples: alternative implementations may employ differing materials.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A facial alignment system for reshaping at least a first facial feature that includes bone or cartilage associated therewith from a current state to a target state, the system comprising:

a first mask portion that includes a first main body portion and a first nose portion, wherein the first main body portion includes first and second cheek portions, wherein the first nose portion is monolithically formed with the first main body portion and the first nose portion protrudes outwardly from the first main body portion, wherein the first mask portion includes a first mask portion pressure zone that is located in the first nose portion, wherein the first mask pressure zone has a first shape that is configured to exert pressure on the first facial feature such that the bone or cartilage associated with the first facial feature is reshaped a first amount, a rear portion, wherein the rear portion includes a tightening mechanism mounted thereon, wherein the tightening mechanism includes first and second tightening members that extend from the rear portion to the first mask portion, and wherein the first and second tightening members are configured to exert a tightening force on the first mask portion, and a second mask portion that includes a second main body portion and a second nose portion, wherein the second main body portion includes first and second cheek portions, wherein the second nose portion is monolithically formed with the second main body portion and the second nose portion protrudes outwardly from the second main body portion, wherein the second mask portion includes a second mask portion pressure zone that is located in the second nose portion, wherein the second mask pressure zone that has a second shape that is configured to exert pressure on the first facial feature such that the bone or cartilage associated with the first facial feature is reshaped a second amount.

2. The facial alignment system of claim 1 wherein the first and second tightening members are removably attached to the first mask portion.

3. The facial alignment system of claim 1 wherein the first mask portion includes first and second connection members, wherein the first tightening member is connected to the first connection member and the second tightening member is connected to the second connection member.

4. The facial alignment system of claim 3 wherein the tightening mechanism includes a rotary dial, wherein when the rotary dial is rotated the first and second tightening members are pulled.

5. The facial alignment system of claim 1 wherein the first mask portion includes a second pressure zone that is not located in the first nose portion.

6. The facial alignment system of claim 1 further comprising a pressure measurement system.

7. The facial alignment system of claim 6 wherein the pressure measurement system includes at least one measurement device secured to an inner surface of at least one of the first mask portion and the rear portion.

8. The facial alignment system of claim 7 wherein the at least one measurement device is positioned in the first mask pressure zone on the first mask portion.

9. The facial alignment system of claim 1 wherein the first mask portion and second mask portion are both made of hard plastic.

10. A method for reshaping a first facial feature that includes bone or cartilage associated therewith from a current state to a target state, the method comprising the steps of:
(a) obtaining a mask assembly that includes a first mask portion and a rear portion, wherein the rear portion includes a tightening mechanism mounted thereon, wherein the tightening mechanism includes first and second tightening members that extend from the rear portion to the first mask portion, wherein the first mask portion includes a first main body portion and a first nose portion, wherein the first main body portion includes first and second cheek portions, wherein the first nose portion is monolithically formed with the first main body portion and the first nose portion protrudes outwardly from the main first body portion, wherein the first mask portion includes a first mask portion pressure zone that is located in the first nose portion, wherein the first mask pressure zone has a first shape that is configured to exert pressure on the first facial feature,
(b) activating the tightening mechanism such that the first and second tightening members exert a tightening force on the first mask portion, wherein the bone or cartilage associated with the first facial feature is reshaped a first amount from the current state to a first interim state,
(c) disconnecting the first mask portion from the rear portion,
(d) obtaining a second mask portion, wherein the second mask portion includes a second main body portion and a second nose portion, wherein the second main body portion includes first and second cheek portions, wherein the second nose portion is monolithically formed with the second main body portion and the second nose portion protrudes outwardly from the second main body portion, wherein the second mask portion includes a second mask portion pressure zone that is located in the second nose portion, wherein the second mask pressure zone has a second shape that is configured to exert pressure on the first facial feature,
(e) connecting the second mask portion to the rear portion, and
(f) activating the tightening mechanism such that the first and second tightening members exert a tightening force on the second mask portion, wherein the bone or cartilage associated with the first facial feature is reshaped a second amount to the target state.

11. The method of claim 10 wherein the tightening mechanism includes a rotary dial, and wherein the method includes rotating the dial to pull the first and second tightening members.

12. The method of claim 11 wherein the first mask portion includes first and second connection portions, wherein during step (a), the first tightening member is removably connected to the first connection portion, and wherein the second tightening member is removably connected to the second connection portion,
wherein during step (c), the method further includes disconnecting the first tightening member from the first connection portion and disconnecting the second tightening member from the second connection portion, wherein the second mask portion includes third and fourth connection portions, and wherein, during step (e), the method further comprises connecting the first tightening member to the third connection portion, and connecting the second tightening member to the fourth connection portion.

* * * * *